United States Patent [19]
Emig et al.

[11] Patent Number: 4,851,420
[45] Date of Patent: Jul. 25, 1989

[54] 2,6-DIAMINO-3-HALOBENZYLPYRIDINES AND PROCESSES FOR THEIR MANUFACTURE AS WELL AS THEIR USE IN PHARMACEUTICALS

[75] Inventors: Peter Emig, Niederdorfelden; Juergen Engel, Alzenau; Gerhard Scheffler, Hanau; Carl H. Weischer, Bonn; Bernd Nickel, Kuehltal, all of Fed. Rep. of Germany

[73] Assignee: ASTA Pharma Aktiengesellschaft, Frankfurt am Main, Fed. Rep. of Germany

[21] Appl. No.: 116,807

[22] Filed: Nov. 5, 1987

[30] Foreign Application Priority Data

Nov. 6, 1986 [DE] Fed. Rep. of Germany ....... 3637829

[51] Int. Cl.$^4$ .................... C07D 213/73; A61K 31/44
[52] U.S. Cl. ...................................... 514/352; 546/307
[58] Field of Search ..................... 546/307; 514/352

[56] References Cited

U.S. PATENT DOCUMENTS 3,954,782  5/1976  Fleckenstein et al. ............. 546/307

FOREIGN PATENT DOCUMENTS 1908078  4/1971  Fed. Rep. of Germany ....... 546/307
1933504  4/1971  Fed. Rep. of Germany ...... 546/307
2514558  10/1975  Fed. Rep. of Germany ...... 546/308

*Primary Examiner*—Alan L. Rotman
*Attorney, Agent, or Firm*—Beveridge, DeGrandi & Weilacher

[57] ABSTRACT

2,6-diamino-3-halobenzylpyridines of the formula I:

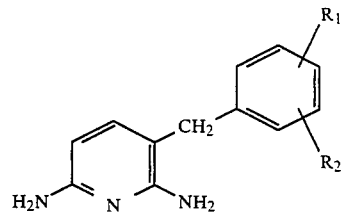

wherein $R_1$ is fluorine and $R_2$ is hydrogen or chlorine as well as their physiologically acceptable acid addition salts, processes for their manufacture and their use in pharmaceuticals.

18 Claims, No Drawings

2,6-DIAMINO-3-HALOBENZYLPYRIDINES AND PROCESSES FOR THEIR MANUFACTURE AS WELL AS THEIR USE IN PHARMACEUTICALS

The present invention relates to novel 2,6-diamino-3-halobenzylpyridines represented by the structural formula (I)

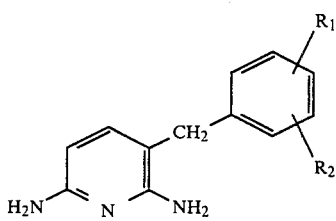

wherein $R_1$ is fluorine and $R_2$ is hydrogen or chlorine, and physiologically acceptable acid addition salts thereof. In a further aspect, the present invention relates to processes for the manufacture of compounds of formula (I) and the use of said compounds in pharmaceuticals.

BACKGROUND OF THE INVENTION

German patent Nos. DE PS 19 33 504 and DE PS 19 08 078 relate to the bactericidal activity of 2-alkylamino-6-aminopyridines. The pharmacological activity of substituted 2,6-diaminopyridines in combating obesity and as antidiabetics is described in German patent specification DOS No. 25 14 558.8. It has now been found that 2,6-diamino-3-halobenzylpyridines of formula I, which are unsubstituted in the 2,6 positions, display analgesic and antipyretic activity.

SUMMARY OF THE INVENTION

These novel compounds may, for example, be prepared by reacting 2,6-diaminopyridine with an arylalkylhalide represented by the structural formula (II):

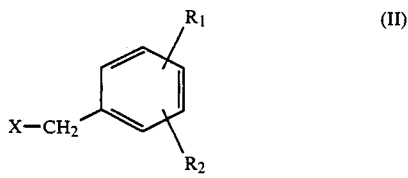

wherein X is halogen, $R_1$ is fluorine and $R_2$ is hydrogen or chlorine.

According to the general process as set forth above this is achieved by slowly heating an equimolar mixture of 2,6-diaminopyridine and an arylalkylhalide of formula II with stirring to about 95° to 110° C. until the mixture begins to melt. The temperature of the melt then rises exothermically without further heating to about 200° to 250° C. and falls again upon completion of the reaction (about 20 minutes). It may be necessary to regulate the course of the exothermic reaction by cooling with ice water. The melt is then stirred for about 2 hours at 130° C. and the reaction mixture is subsequently cooled to 25° C. and dissolved in a mixture of 400 ml of methylene chloride and about 40 ml of concentrated ammonia. This solution is extracted twice with 150 ml of water, the organic phase is separated off, dried over anhydrous sodium sulphate and then concentrated in a vacuum. The remaining residue is separated using column chromatography techniques (Geduran Si 60 from Merck) with an eluting solvent which is methylene chloride/methanol or ethanol. The reaction products are isolated according to their different flow speeds. In general the reaction proceeds within the temperature range of 50° to 300° C. The pure compounds obtained are in the form of bases. They may if desired, be converted into therapeutically acceptable salts by reaction with acids.

Acids which may be used include for example: hydrohalic acids, sulphuric acid, phosphoric acids, nitric acid, perchloric acid, organic mono-, di- or tricarboxylic acids of the aliphatic, alicyclic, aromatic or heterocyclic series as well as sulfonic acids. Examples of these are: formic, acetic, propionic, succinic, glycolic, lactic, malic, tartaric, citric, ascorbic, maleic, fumaric, hydroxymaleic, gluconic or pyruvic acid; phenylacetic, benzoic, p-aminosalicyclic acid, embonic acid, methanesulfonic, ethanesulphonic, hydroxyethanesulfonic, ethylenesulphonic acid; halobenzenesulphonic, toluenesulfonic, naphthalenesulfonic acid or sulfanilic acid or also 8-chloro-theophylline.

A preferred method of carrying out the same reaction comprises melting a molar amount of 2,6-diaminopyridine by slow heating and then adding dropwise an equimolar amount of a liquid arylalkylhalide at 100° to 130° C., preferably at 115° to 120° C. The temperature then rises exothermically to about 140° to 160° C. Heating is continued for about a further 4 hours at 130° to 150° C., after which the mixture is cooled and the syrupy mixture is dissolved in 400 ml of methylene chloride and about 40 ml of concentrated ammonia.

The working up and the column chromatographic separation of the reaction products is carried out as described above.

The compounds of formula I may also be prepared, for example, by reacting 2,6 diaminopyridine with an arylalkylamine represented by the structural formula (III):

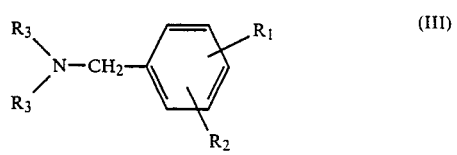

wherein $R_3$ is $C_1$–$C_4$ alkyl, $R_1$ is fluorine and $R_2$ is hydrogen or chlorine, in the presence of alkali metal alcoholate.

Alkali metal alcoholates which may be used are the sodium or potassium salts of lower aliphatic $C_1$–$C_4$ alcohols.

At least a four times molar excess of the 2,6-diaminopyridine is used in order to minimize formation of the side products disubstituted in the 3,5 positions of the pyridine ring and the N-benzylated side products of 2,6-diamino-pyridine. The reaction is carried out in an inert organic solvent at temperatures between 100° and 150° C. in an inert gas atmosphere such as $N_2$ according to the method of B. S. Rauckman and B. Roth, J. Med. Chem. 23, 384, 1980. Solvents which may be used are, for example, lower $C_1$–$C_4$ alcohols, lower diols, lower $C_1$–$C_4$ ethers, lower cyclic ethers such as for example methoxyethanol, dioxan, ethylene glycol, etc. The working up and column chromatographic separation of the reaction products is also effected in the above-described manner.

In a further process a solution of 2,6-diaminopyridine and the same or twice the molar amount of arylakylhalide in a polar inert organic solvent is heated to 90°–110° C. or at the boiling temperature of the solvent for 8 hours under nitrogen, the solvent is distilled off after cooling the reaction mixture and the residue remaining is worked up in the above-mentioned manner and purified by column chromatography.

Solvents which may be used for this reaction are for example: lower aliphatic ketones such as for example acetone, methylethyl ketone; halogenated hydrocarbons such as for example chloroform, carbon tetrachloride, chlorobenzene, methylene chloride; cyclic ethers such as for example tetrahydrofuran and dioxan; lower aliphatic acyclic ethers (diethylether, diisopropylether); lower aliphatic alcohols (1–6 carbon atoms), such as for example methanol, ethanol, isopropanol, amylalcohol, butanol, tert-butanol; $C_1$–$C_4$-alkoxy-substituted alcohols (methoxyethanol) amides and N-alkyl-substituted amides of aliphatic $C_1$–$C_4$-carboxylic acids (dimethylformamide, dimethylacetamide); $C_1$–$C_6$-dialkylsulfones (dimethylsulfone, tetramethylsulfone); $C_1$–$C_6$-dialkylsulfoxides (dimethylsulfoxide), di- and polyfunctional aliphatic alcohols (ethylene glycol) as well as other aprotic agents such as N-methyl pyrrolidone, tetramethyl urea, hexamethylphosphoric acid triamide, acetonitrile and propionitrile.

The individual alkyl radicals of the above-mentioned solvents may contain, for example, 1–6, in particular 1–4 carbon atoms. It is also possible to use mixtures of these agents as well as mixtures with water as the reaction medium.

The phenyl ring of the compounds of formula I prepared according to this process is preferably ortho and/or para substituted with halogen. The halogen atom ($R_1$ and $R_2$) is preferably fluorine and/or chlorine. 2,6-diamino-3-(4-fluoro)-benzylpyridine and physiologically acceptable salts of addition thereof display particularly favourable characteristics.

DETAILED DESCRIPTION OF THE INVENTION

The following compounds of formula I are prepared according to the methods of preparation given above.

| | | | |
|---|---|---|---|
| D 17033 | $R_1$ = p-fluoro | $R_2$ = H | M.p.: 123–124° C. |
| D 17746 | $R_1$ = o-fluoro | $R_2$ = H | M.p.: 115–117° C. |
| D 17748 | $R_1$ = o-fluoro | $R_2$ = o-chloro | M.p.: 108–111° |

In animal experiments, the compounds of formula I, and their physiologically acceptable acid addition salts display valuable therapeutic properties in particular central and peripheral analgesic as well as antipyretic characteristics. In particular, compound D 17033 is characterized by a general absence of side-effects such as for example gastrointestinal disorders and gastric ulcers as compared to known substances, such as for example non-steroidal anti-inflammatory agents with analgesic components.

The active substances of the invention and their salts may be converted into the conventional pharmaceutical forms of application such as tablets, coated tablets, solutions, emulsions, powders, capsules or depot forms, whereby it is possible to use the conventional pharmaceutical auxiliary substances as well as the conventional production methods for their manufacture. Suitable tablets may for example be obtained by mixing the active ingredients with known inert ingredients, for example inert diluting agents such as calcium carbonate, calcium phosphate or lactose, disintegrating agents such as maize starch or alginic acid, binding agents such as starch or gelatine, lubricants such as magnesium stearate or talcum and/or agents for achieving a depot effect such as carboxypolymethylene, carboxymethyl cellulose, celluloseacetate phthalate or polyvinyl acetate.

The tablets may also be composed of several layers. Coated tablets may correspondingly be prepared by coating cores produced in analagous manner to the tablets with agents conventionally used for coating coated tablets, such as collidon or shellac, gum arabic, talcum, titanium dioxide or sugar. To achieve a depot effect, or to avoid incompatibilities, the core may be composed of several layers. Similarly, the coating of the coated tablet may consist of several layers in order to achieve a depot effect, whereby the inactive ingredients mentioned above in connection with the tablets may be used.

Liquid formulations of the active ingredients of the invention, or combination of active ingredients may, in addition, contain a sweetening agent such as saccharine, cyclamate, glycerine or sugar, as well as a flavour enhancing agent, for example aromatic substances such as vanillin or orange extract.

They may also contain suspending or thickening agents such as sodium carboxymethyl cellulose, wetting agents such as condensation products of fatty alcohols with ethylene oxide or preservatives such as p-hydroxybenzoates.

Injectable solutions are produced in the conventional manner, for example with the addition of preservatives such as p-hydroxybenzoates, or stabilizers, such as complexing agents, and filled into injection vials or ampoules.

Capsules containing the active ingredients or combinations of active ingredients may for example be manufactured by mixing the active ingredients with inert carriers such as lactose or sorbitol and encapsulating them in gelatine capsules.

Suitable suppositories may for example be produced by mixing the active ingredients or combinations of active ingredients intended for that purpose with conventional carriers such as neutral fats or polyethylene glycol or its derivatives. The product may also be administered by a nasal spray, if desired.

The following examples are illustrations of the present invention:

EXAMPLE 1

2,6-diamino-3-(4-fluoro)benzylpyridine (D 17033)

10.9 g (0.1M) of 2,6-diaminopyridine are melted by gradual warming and 14.45 g (0.1M) of 4-fluorobenzylchloride are added dropwise at 115°–120° C. After the reaction has heated exothermically up to about 140°–160° C., heating is continued for a further approximately 4 hours at 130°–150° C., after which the reaction vessel is cooled and the syrupy mixture is dissolved in 400 ml of methylene chloride and about 40 ml of concentrated ammonia. The reaction mixture is extracted with water and the organic phase is then separated off and dried over anhydrous sodium sulphate. The solvent is evaporated off in a vacuum and the remaining residue is separated by column chromatography (Geduran Si 60 from Merck AG, Darmstadt, eluting solvent: methylene chloride/ethanol—9:1% by volume). There are obtained 12.6 g of 2,6-diamino-3-(4-fluoro)benzylpyridine with a melting point of 123°–124° C. (Yield 58% of theory). Thin layer chromatography: $R_F$-value: 0.34 Eluting solvent: methylene chloride/ethanol/concentrated ammonia=95:4:1% by volume).

Following evaporation of the solvent, the remaining residue may also be purified by fractionated distillation in a high vacuum (B.p.: 190°–210° C. at 0.4 m bar)

EXAMPLE 2

2,6-diamino-3-(4-fluoro)benzylpyridine maleate 3.12 g of 2,6-diamino-3-(4-fluoro)benzylpyridine are dissolved in 33 ml of methylene chloride and fractionally precipitated with a solution of 1.66 g of maleic acid in ether. The crystalline maleate that is formed overnight is filtered under suction, washed with ice-cooled methylene chloride and the precipitate is suspended in about 15 ml of ether. Filtration yields 3.6 g of 2,6-diamino-3-(4-fluoro)benzylpyridine maleate. By recrystallization from warm ethanol one obtains by means of thin layer chromatography (thin layer chromatography on silica gel prepared plates 60 $F_{254}$ from Merck AG, eluent: methylene chloride/ethanol 9:1, development by fluorescence in UV light and iodine vapour, $R_F=0.5$) 3 g of standardized 2,6-diamino-3-(4-fluoro)-benzylpyridine maleate. M.p.: 161°–162° C.

EXAMPLE 3

2,6-diamino-3-(4-fluoro)benzylpyridine hydrochloride (D 19 605)

1.51 g of 2,6-diamino-3-(4-fluoro)benzylpyridine are dissolved in 47 ml of methylene chloride and the solution is mixed dropwise under argon inert gas with 1.31 ml of 5.42N isopropanolic hydrochloric acid while stirring thoroughly. Crystallization of the HCl salt commences after about 10 minutes. Stirring continues for about 1.5 hours at room temperature, after which one suction filters under argon, washes twice with 2 ml of methylene chloride in each case and suspends the crude crystals under stirring in 15 ml of ether. After 1.5 hours the product is suction filtered and dried at 40° C. in a vacuum.

Yield: 1.6 g, M.p.: 164°–167° C.

The same procedure is followed to produce:

2,6-diamino-3-(2-fluoro)benzylpyridine (D 17 746)
M.p.: 115°–117° C., Yield 62% of theory.
Column chromatography: eluting solvent methylene chloride/ethanol=9:1% by volume)
Thin layer chromatography: $R_F$—value: 0.56
Eluting solvent: methylene chloride/ethanol/concentrated ammonia—90:10:1% by volume
2,6-diamino-3-(2-fluoro-6-chloro)benzylpyridine (D 17 748)
Melting point: 108°–111° C. Yield: 55% of theory Column chromatography: eluting solvent methylene chloride/ethanol=9:1% by volume.

Thin layer chromatography: $R_F$—value: 0.31
Eluting solvent: methylene chloride/ethanol/concentrated ammonia=95:44:1% by volume.

EXAMPLE 4

2,6-diamino-3-(4-fluoro)benzylpyridine (D 17 033)

A mixture of 34.9 g (0.32M) of 2,6-diaminopyridine, 12.2 g (0.08M) of N,N-dimethyl-N-(4-fluorobenzyl)amine and 0.65 g (0.012M) of sodium methylate are heated in 190 ml of ethylene glycol in a nitrogen atmosphere to 120° C. Following a reaction time of 2½ hours the mixture is cooled to room temperature and 9 ml of glacial acetic acid are added to the mixture. The solvent is then removed under vacuum and the remaining residue is taken up in methanol and treated with animal charcoal. Following filtration of the animal charcoal, the residue is purified using column chromatography as in Example 1. There are obtained 8.5 g of 2,6-diamino-3-(4-fluoro)benzylpyridine (Yield: 49% of theory).

Novel 2,6-diamino-3-halobenzylpyridines

Compounds:

[Structure of 2,6-diamino-3-benzylpyridine with substituents $R_1$ and $R_2$ on the phenyl ring]

| | $R_1$ | $R_2$ | M.p. |
|---|---|---|---|
| D 17033 | p-fluoro | H | 123–124° C. |
| D 17746 | o-fluoro | H | 115–117° C. |
| D 17748 | o-fluoro | o-chloro | 108–111° C. |

The pharmaceutical data set out below shows the valuable properties of the new compounds of formula I in comparison to a known analgesic

| Compound | acetic acid Writhing Test Mouse $ED_{50}$ mg/kg p.a. | Randall-Selitto Test Rat $ED_{50}$ mg/kg p.o at $ED_{50}$ mg/kg |
|---|---|---|
| D 17033 | 1.4 | 0.2 |
| D 17748 | 0.5/34% | 0.5/57% |
| Flupirtin (Katadolon (R)) | 44.5 | 38.8 |

Literature:

Acetic acid Writhing Test Koster et al., Fed. Proc., Volume 18, 412 (1959).

Randall-Selitto Test G. Engelhardt, Arzneim. Forsch. 34, 992 et seq. (1984); Maruyama et al., Arzneim. Forsch. 28, 11 (1978).

Toxicity $LD_{50}$ Rat $LD_{50}$ Mouse mg/kp p.o. mg/kg p.o.

D 17033, 1100, 266
D 17746 276
D 17748 285 Flupirtin
(Katadolon (R)) 1660 633

Literature:

Miller, Tainter, Proc. Soc. Exper. Biol. Med. 57, 261 (1944).

The toxicity of the compounds of the invention in animal experiments is less than that of the known commercial preparation Flupirtin (Katadolon (R)).

Further variations and modifications will be apparent to those skilled with art from the foregoing and are intended to be encompassed by the appended claims.

German priority application No. P 3637829.1 is relied on and incorporated by reference.

We claim:

1. A compound which is a 2,6-Diamino-3-halobenzyl pyridine represented by the structural formula (I):

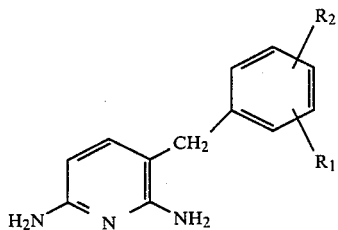

wherein $R_1$ is fluorine and $R_2$ is hydrogen or chlorine, or a physiologically acceptable acid addition salt thereof.

2. The compound according to claim 1 wherein $R_1$=p-fluoro and $R_2$=H.
3. The compound according to claim 1 wherein $R_1$=o-fluoro and $R_2$=H.
4. The compound according to claim 1 wherein $R_1$=o-fluoro and $R_2$=o-chloro.
5. A process for the preparation of a 2,6-diamino-3-halobenzyl pyridine of formula I or a physiologically acceptable acid addition salt thereof,

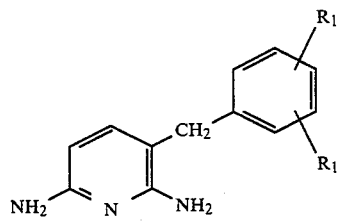

wherein $R_1$ is fluorine and $R_2$ is hydrogen or chlorine, comprising:
reacting 2,6-diaminopyridine with an arylalkylhalide of the formula II:

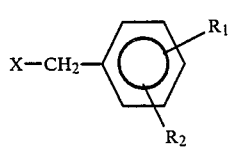

wherein X is halogen and $R_1$ is fluorine and $R_2$ is hydrogen or chlorine.

6. The process according to claim 5 wherein 2,6-diaminopyridine and said arylalkylhalide are heated to about 95° to 110° C. with stirring to melt the mixture, permitting the temperature of the reaction to rise to not more than about 250° C., cooling the reaction mixture and dissolving the reaction mixture in an organic solvent containing concentrated ammonia, extracting with water, separatinng the organic phase, drying, concentrating and obtaining the product by column chromatography.

7. The process according to claim 5 wherein 2,6-diaminopyridine and said arylalkyl halide are heated to 100° to 130°, until an exothermic heating takes place to about 140° to 160° C., thereafter continuing heating at 130° to 150° C., cooling the mixture to obtain a syrupy mixture, dissolving said mixture in an inert organic solvent and concentrated ammonia, and recovering the product by column chromatography.

8. A process in accordance with claim 5 wherein the said pyridine and said halide are heated and thereafter cooled to obtain a reaction mixture, the reaction mixture is cooled in an organic solvent, the organic phase is separated and the product is recovered.

9. An analgesic or antipyretic composition comprising an analgesic or antipyretic effective amount of a compound represented by the structural formula I:

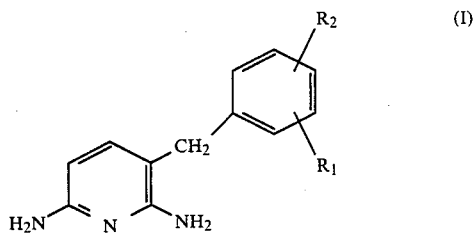

wherein $R_1$ is fluorine and $R_2$ is hydrogen or chloride, or a physiologically acceptable acid salt of addition thereof, and a physiologically acceptable carrier.

10. The therapeutic composition according to claim 9 in the form of a tablet.
11. The therapeutic composition according to claim 9 wherein the compound is:
2,6-diamino-3-(4-fluoro)benzylpyridine.
12. The therapeutic composition according to claim 9 wherein the compound is:
2,6-diamino-3-(4-fluoro)benzylpyridine hydrochloride.
13. The therapeutic composition according to claim 9 wherein the compound is:
2,6-diamino-3-(2-fluoro)benzylpyridine.
14. The therapeutic composition according to claim 9 wherein the compound is:
2,6-diamino-3-(2-fluoro-6-chloro)benzylpyridine.
15. A method for treating a warm blooded mammal for treatment of pain affecting the organism, comprising administering to said mammal an analgesic or antipyretic effective amount of a compound of formula I or physiologically acceptable acid addition salt thereof as defined in claim 1.
16. A method for treating a warm blooded mammal for treatment of fever affecting the organism comprising administering to said mammal an antipyretic effective amount of a compound of formula I or a physiologically acceptable acid addition salt thereof as defined in claim 1.
17. A process for the preparation of a 2,6-diamino-3-halobenzyl pyridine of formula I or a physiologically acceptable acid addition salt thereof,

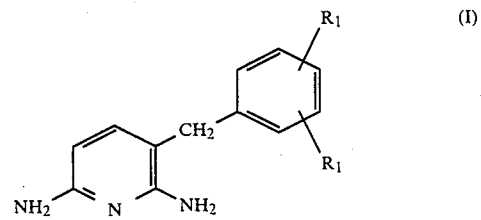

wherein $R_1$ is fluorine and $R_2$ is hydrogen or chlorine, comprising:

reacting 2,6-diaminopyridine with an arylalkylamine of formula III:

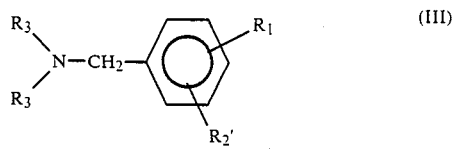

wherein $R_3$ is $C_1$–$C_4$ alkyl and $R_1$ is fluorine and $R_2$ is hydrogen or chlorine, in the presence of an alkali metal alcoholate.

18. The process according to claim 17 wherein 2,6-diaminopyridine and said arylalkylamine are reacted in the presence of an alkali metal alcoholate, the pyridine compound being present in four times molar excess, and in the presence of an inert organic solvent at a temperature of about 100° to 150° C. under an inert gas atmosphere.

* * * * *